(12) United States Patent
Auld

(10) Patent No.: US 10,188,506 B2
(45) Date of Patent: *Jan. 29, 2019

(54) INTRAOCULAR LENS INSERTER

(71) Applicant: ALCON PHARMACEUTICALS LTD., Fribourg (CH)

(72) Inventor: Jack R. Auld, Lake Forest, CA (US)

(73) Assignee: Alcon Pharmaceuticals, Ltd., Case Postale, Fribourg (CH)

(*) Notice: Subject to any disclaimer, the term of this patent is extended or adjusted under 35 U.S.C. 154(b) by 205 days.

This patent is subject to a terminal disclaimer.

(21) Appl. No.: 14/679,921

(22) Filed: Apr. 6, 2015

(65) Prior Publication Data
US 2016/0067036 A1    Mar. 10, 2016

Related U.S. Application Data

(63) Continuation of application No. 14/291,743, filed on May 30, 2014, now Pat. No. 8,998,983, which is a
(Continued)

(51) Int. Cl.
*A61F 2/16* (2006.01)
*A61F 9/007* (2006.01)

(52) U.S. Cl.
CPC ............ *A61F 2/167* (2013.01); *A61F 2/1662* (2013.01); *A61F 2/1678* (2013.01); *A61F 9/007* (2013.01)

(58) Field of Classification Search
CPC ... A61M 5/2053; A61F 2/1662; A61F 2/1664; A61F 2/1667; A61F 2/167; A61F 2/1672; A61F 2/1675; A61F 2/1678; A61F 2002/1681; A61F 2002/1682; A61F 2002/16905; A61F 2/1691; A61F 9/007; A61F 2/95; A61F 2002/9517;
(Continued)

(56) References Cited

U.S. PATENT DOCUMENTS

| | | |
|---|---|---|
| 2,547,099 A | 4/1951 | Smoot |
| 4,429,421 A | 2/1984 | Levy |

(Continued)

FOREIGN PATENT DOCUMENTS

| | | |
|---|---|---|
| CA | 2858485 A1 | 6/2013 |
| EP | 174129 A1 | 3/1986 |

(Continued)

OTHER PUBLICATIONS

International Search Report and Written Opinion in Application No. PCT-US2013-044183 dated Nov. 4, 2013 in 15 pages.
(Continued)

*Primary Examiner* — David C Eastwood

(57) ABSTRACT

An intraocular lens inserter can include an energy storage portion, an actuator portion, and a lens support portion. The energy storage portion can include a compressible energy storage device, such as a compressible fluid, springs, and other devices. The inserter can include an actuator portion operating with a substantially incompressible fluid, such as liquids or other noncompressible fluids. The actuator can be configured to provide an operator with control over the release of energy from the energy storage portion so as to move a plunger for the discharge of a lens from an intraocular lens cartridge.

29 Claims, 10 Drawing Sheets

Related U.S. Application Data continuation of application No. PCT/US2013/044183, filed on Jun. 4, 2013.

(60) Provisional application No. 61/655,255, filed on Jun. 4, 2012.

(58) Field of Classification Search
CPC ...... A61F 2002/9528; A61F 2002/9522; A61F 2002/9534; A61F 2/954; A01K 11/00; A01K 11/001; A01K 11/006; A01K 11/008; A01K 11/007
USPC ...... 606/107–108; 623/6.11–6.13; 604/8–10, 604/57, 59–60, 187
See application file for complete search history.

(56) References Cited

U.S. PATENT DOCUMENTS

| | | |
|---|---|---|
| 4,573,998 A | 3/1986 | Mazzocco |
| 4,615,703 A | 10/1986 | Callahan et al. |
| 4,619,256 A | 10/1986 | Horn |
| 4,634,423 A | 1/1987 | Bailey, Jr. |
| 4,699,140 A | 10/1987 | Holmes et al. |
| 4,715,373 A | 12/1987 | Mazzocco et al. |
| 4,726,367 A | 2/1988 | Shoemaker |
| 4,747,404 A | 5/1988 | Jampel et al. |
| 4,763,650 A | 8/1988 | Hauser |
| 4,765,329 A | 8/1988 | Cumming et al. |
| 4,822,360 A | 4/1989 | Deacon |
| 4,844,065 A | 7/1989 | Faulkner |
| 4,844,093 A | 7/1989 | Jampel et al. |
| 4,852,566 A | 8/1989 | Callahan et al. |
| 4,862,885 A | 9/1989 | Cumming |
| 4,880,000 A | 11/1989 | Holmes et al. |
| 4,906,247 A | 3/1990 | Fritch |
| 4,919,130 A | 4/1990 | Stoy et al. |
| 4,934,363 A | 6/1990 | Smith et al. |
| 5,007,913 A | 4/1991 | Dulebohn et al. |
| 5,064,413 A * | 11/1991 | McKinnon .............. A61M 5/30 604/143 |
| 5,066,297 A | 11/1991 | Cumming |
| 5,098,439 A | 3/1992 | Hill et al. |
| 5,123,905 A | 6/1992 | Kelman |
| 5,222,972 A | 1/1993 | Hill et al. |
| 5,190,552 A | 3/1993 | Kelman |
| 5,304,182 A | 4/1994 | Rheinish et al. |
| 5,354,333 A | 10/1994 | Kammann et al. |
| 5,496,328 A | 3/1996 | Nakajima et al. |
| 5,562,676 A | 10/1996 | Brady et al. |
| 5,582,613 A | 12/1996 | Brady et al. |
| 5,582,614 A | 12/1996 | Feingold |
| 5,607,433 A | 3/1997 | Polla et al. |
| 5,616,148 A | 4/1997 | Eagles et al. |
| 5,629,577 A | 5/1997 | Polla et al. |
| 5,630,821 A | 5/1997 | Klaas |
| 5,643,275 A | 7/1997 | Blake |
| 5,643,276 A | 7/1997 | Zaleski |
| 5,693,057 A | 12/1997 | Dusek |
| 5,716,364 A | 2/1998 | Makker et al. |
| 5,772,666 A | 6/1998 | Feingold et al. |
| 5,772,667 A | 6/1998 | Blake |
| 5,776,138 A | 7/1998 | Vidal et al. |
| 5,800,441 A | 9/1998 | Polla et al. |
| 5,803,925 A | 9/1998 | Yang et al. |
| 5,807,400 A | 9/1998 | Chambers et al. |
| 5,810,833 A | 9/1998 | Brady et al. |
| 5,860,984 A | 1/1999 | Chambers et al. |
| 5,868,751 A | 2/1999 | Feingold |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,921,989 A | 6/1999 | Deacon et al. |
| 5,944,725 A | 8/1999 | Cicenas et al. |
| 5,947,975 A | 9/1999 | Kikuchi et al. |
| 5,947,976 A | 9/1999 | Van Noy et al. |
| 6,042,587 A | 3/2000 | Polla et al. |
| 6,162,230 A | 12/2000 | Polla et al. |
| 6,299,618 B1 | 10/2001 | Sugiura |
| 6,312,433 B1 | 11/2001 | Butts et al. |
| 6,334,862 B1 | 1/2002 | Vidal et al. |
| 6,336,932 B1 | 1/2002 | Figueroa et al. |
| 6,342,058 B1 | 1/2002 | Portney |
| 6,371,960 B2 | 4/2002 | Heyman et al. |
| 6,387,101 B1 | 5/2002 | Butts et al. |
| 6,398,789 B1 | 6/2002 | Capetan |
| 6,428,545 B2 | 8/2002 | Portney |
| 6,468,282 B2 | 10/2002 | Kikuchi et al. |
| 6,491,697 B1 | 12/2002 | Clark et al. |
| 6,500,181 B1 | 12/2002 | Portney |
| 6,500,239 B2 | 12/2002 | Castellano et al. |
| 6,503,275 B1 | 1/2003 | Cumming |
| 6,506,195 B2 | 1/2003 | Chambers et al. |
| 6,537,281 B1 | 3/2003 | Portney |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,592,591 B2 | 7/2003 | Polla et al. |
| 6,607,537 B1 | 8/2003 | Binder |
| 6,629,979 B1 | 10/2003 | Feingold et al. |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,037,328 B2 | 5/2006 | Vincent |
| 7,131,976 B2 | 11/2006 | Kobayashi et al. |
| 7,137,994 B2 | 11/2006 | De Juan, Jr. et al. |
| 7,156,854 B2 | 1/2007 | Brown et al. |
| 7,156,855 B2 | 1/2007 | Oda |
| 7,276,071 B2 | 10/2007 | Lin et al. |
| 7,279,006 B2 | 10/2007 | Vincent |
| 7,335,209 B2 | 2/2008 | Meyer |
| RE40,185 E | 3/2008 | Kikuchi et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,229 B2 | 1/2009 | Meyer |
| 7,476,230 B2 | 1/2009 | Ohno et al. |
| 7,645,300 B2 | 1/2010 | Tsai |
| 7,687,097 B2 | 3/2010 | Makker et al. |
| 7,704,258 B2 | 4/2010 | Feingold et al. |
| 7,717,879 B2 | 5/2010 | Mansouri |
| 7,740,607 B2 | 6/2010 | Willis et al. |
| 7,740,636 B2 | 6/2010 | Lee et al. |
| 7,744,603 B2 | 6/2010 | Zadno-Azizi et al. |
| 7,867,240 B2 | 1/2011 | Peterson et al. |
| 7,892,283 B2 | 2/2011 | Shepherd |
| 7,901,414 B2 | 3/2011 | Tourrette et al. |
| 7,947,049 B2 | 5/2011 | Vaquero |
| 7,988,701 B2 | 8/2011 | Vaquero et al. |
| 8,021,423 B2 | 9/2011 | Tanaka |
| 8,048,085 B2 | 11/2011 | Peterson et al. |
| 8,062,360 B2 | 11/2011 | Pollock |
| 8,080,017 B2 | 12/2011 | Tanaka |
| 8,114,095 B2 | 2/2012 | Rathert |
| 8,123,719 B2 | 2/2012 | Edwards et al. |
| 8,123,804 B2 | 2/2012 | Tanaka |
| 8,142,498 B2 | 3/2012 | Tsai |
| 8,152,817 B2 | 4/2012 | Tanaka |
| 8,216,629 B2 | 7/2012 | Mentak |
| 8,225,643 B2 | 7/2012 | Abboud et al. |
| 8,246,631 B2 | 8/2012 | Pynson |
| 8,252,053 B2 | 8/2012 | Pynson |

(56) References Cited

U.S. PATENT DOCUMENTS

| | | |
|---|---|---|
| 8,308,736 B2 | 11/2012 | Boukhny et al. |
| 8,308,799 B2 | 11/2012 | Chen et al. |
| 8,500,681 B2 | 8/2013 | Gonnelli et al. |
| 8,574,196 B2 | 11/2013 | Stammen et al. |
| 8,579,969 B2 | 11/2013 | Zacharias |
| 8,617,099 B2 | 12/2013 | Williamson |
| 8,657,835 B2 | 2/2014 | Boukhny et al. |
| 8,668,734 B2 | 3/2014 | Hildebrand et al. |
| 8,721,702 B2 | 5/2014 | Ramada et al. |
| 8,758,433 B2 | 6/2014 | Cole et al. |
| 8,956,408 B2 | 2/2015 | Smiley et al. |
| 8,968,396 B2 | 3/2015 | Matthews et al. |
| 8,998,983 B2 * | 4/2015 | Auld ............... A61F 2/1678 606/107 |
| 9,228,273 B2 | 1/2016 | Keszler et al. |
| 9,255,665 B2 | 2/2016 | Brouillette et al. |
| 2001/0007075 A1 | 7/2001 | Hjertman et al. |
| 2001/0007942 A1 | 7/2001 | Kikuchi et al. |
| 2001/0015593 A1 | 8/2001 | Polla et al. |
| 2002/0193803 A1 | 12/2002 | Portney |
| 2003/0187455 A1 | 10/2003 | Kobayashi et al. |
| 2003/0212406 A1 | 11/2003 | Kobayashi et al. |
| 2003/0212407 A1 | 11/2003 | Kikuchi et al. |
| 2003/0216745 A1 | 11/2003 | Brady et al. |
| 2004/0059343 A1 | 3/2004 | Shearer et al. |
| 2004/0127911 A1 | 7/2004 | Figueroa et al. |
| 2004/0215207 A1 | 10/2004 | Cumming |
| 2004/0267359 A1 | 12/2004 | Maker et al. |
| 2005/0033308 A1 | 2/2005 | Callahan et al. |
| 2005/0171555 A1 | 8/2005 | Tran et al. |
| 2005/0222577 A1 | 10/2005 | Vaquero |
| 2005/0267403 A1 | 12/2005 | Landau et al. |
| 2005/0283162 A1 | 12/2005 | Stratas |
| 2005/0283163 A1 | 12/2005 | Portney et al. |
| 2005/0283164 A1 | 12/2005 | Wu et al. |
| 2006/0085013 A1 | 4/2006 | Dusek et al. |
| 2006/0129125 A1 | 6/2006 | Copa et al. |
| 2006/0142780 A1 | 6/2006 | Pynson et al. |
| 2006/0142781 A1 | 6/2006 | Pynson et al. |
| 2006/0167466 A1 | 7/2006 | Dusek |
| 2006/0184181 A1 | 8/2006 | Cole et al. |
| 2006/0264971 A1 | 11/2006 | Akahoshi |
| 2006/0271063 A1 | 11/2006 | Sunada et al. |
| 2006/0287655 A1 | 12/2006 | Khuray et al. |
| 2006/0293694 A1 | 12/2006 | Futamura |
| 2007/0060925 A1 | 3/2007 | Pynson |
| 2007/0112355 A1 | 5/2007 | Salahieh et al. |
| 2007/0203502 A1 | 8/2007 | Makker et al. |
| 2007/0270881 A1 | 11/2007 | Hishinuma et al. |
| 2007/0270945 A1 | 11/2007 | Kobayashi et al. |
| 2008/0004610 A1 | 1/2008 | Miller et al. |
| 2008/0027460 A1 | 1/2008 | Kobayashi |
| 2008/0027461 A1 | 1/2008 | Vaquero et al. |
| 2008/0033449 A1 | 2/2008 | Cole et al. |
| 2008/0039862 A1 | 2/2008 | Tran |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0097460 A1 | 4/2008 | Boukhny et al. |
| 2008/0097461 A1 | 4/2008 | Boukhny et al. |
| 2008/0114203 A1 | 5/2008 | Crank |
| 2008/0119783 A1 | 5/2008 | Green |
| 2008/0147080 A1 | 6/2008 | Pynson |
| 2008/0147081 A1 | 6/2008 | Pynson |
| 2008/0147082 A1 | 6/2008 | Pynson |
| 2008/0154361 A1 | 6/2008 | Pynson et al. |
| 2008/0171968 A1 | 7/2008 | Stout et al. |
| 2008/0208176 A1 | 8/2008 | Loh |
| 2008/0255579 A1 | 10/2008 | Wollenhaupt et al. |
| 2008/0269770 A1 | 10/2008 | Pynson et al. |
| 2009/0005788 A1 | 1/2009 | Rathert |
| 2009/0018548 A1 | 1/2009 | Charles |
| 2009/0024136 A1 | 1/2009 | Martin et al. |
| 2009/0030425 A1 | 1/2009 | Smiley et al. |
| 2009/0036898 A1 | 2/2009 | Ichinohe et al. |
| 2009/0043313 A1 | 2/2009 | Ichinohe et al. |
| 2009/0112222 A1 | 4/2009 | Barrows et al. |
| 2009/0198247 A1 | 8/2009 | Ben Nun |
| 2009/0204122 A1 | 8/2009 | Ichinohe et al. |
| 2009/0234366 A1 | 9/2009 | Tsai et al. |
| 2009/0248031 A1 | 10/2009 | Ichinohe et al. |
| 2009/0270876 A1 | 10/2009 | Hoffmann et al. |
| 2009/0292293 A1 | 11/2009 | Bogaert et al. |
| 2009/0318933 A1 | 12/2009 | Anderson |
| 2010/0010498 A1 | 1/2010 | Biddle et al. |
| 2010/0057095 A1 | 3/2010 | Khuray et al. |
| 2010/0076450 A1 | 3/2010 | Yoshida et al. |
| 2010/0082037 A1 | 4/2010 | Kobayashi et al. |
| 2010/0087832 A1 | 4/2010 | Seyboth |
| 2010/0094309 A1 | 4/2010 | Boukhny et al. |
| 2010/0106160 A1 | 4/2010 | Tsai |
| 2010/0121340 A1 | 5/2010 | Downer |
| 2010/0125278 A1 | 5/2010 | Wagner |
| 2010/0125279 A1 | 5/2010 | Karakelle et al. |
| 2010/0160926 A1 | 6/2010 | Artsyukhovich et al. |
| 2010/0161049 A1 | 6/2010 | Inoue |
| 2010/0185206 A1 | 7/2010 | Ichinohe et al. |
| 2010/0204704 A1 | 8/2010 | Davies et al. |
| 2010/0204705 A1 | 8/2010 | Brown et al. |
| 2010/0217273 A1 | 8/2010 | Someya et al. |
| 2010/0217274 A1 | 8/2010 | Lee et al. |
| 2010/0228260 A1 | 9/2010 | Callahan et al. |
| 2010/0228261 A1 | 9/2010 | Feingold et al. |
| 2010/0256651 A1 | 10/2010 | Jani et al. |
| 2010/0280521 A1 | 11/2010 | Vaquero et al. |
| 2010/0286704 A1 | 11/2010 | Ichinohe et al. |
| 2010/0305577 A1 | 12/2010 | Muchhala et al. |
| 2010/0312254 A1 | 12/2010 | Downer et al. |
| 2011/0046633 A1 | 2/2011 | Pankin et al. |
| 2011/0046634 A1 | 2/2011 | Rathert |
| 2011/0046635 A1 | 2/2011 | Pankin et al. |
| 2011/0082463 A1 | 4/2011 | Inoue |
| 2011/0098717 A1 | 4/2011 | Inoue |
| 2011/0144653 A1 | 6/2011 | Pankin et al. |
| 2011/0152872 A1 | 6/2011 | Seyboth et al. |
| 2011/0152873 A1 | 6/2011 | Shepherd |
| 2011/0172676 A1 | 7/2011 | Chen |
| 2011/0190777 A1 | 8/2011 | Hohl |
| 2011/0213380 A1 | 9/2011 | Han |
| 2011/0224677 A1 | 9/2011 | Niwa et al. |
| 2011/0245840 A1 | 10/2011 | Seyboth et al. |
| 2011/0264101 A1 | 10/2011 | Inoue et al. |
| 2011/0264102 A1 | 10/2011 | Cole et al. |
| 2011/0264103 A1 | 10/2011 | Cole et al. |
| 2011/0270264 A1 | 11/2011 | Shoji et al. |
| 2011/0288557 A1 | 11/2011 | Kudo et al. |
| 2011/0295264 A1 | 12/2011 | Cole et al. |
| 2011/0313425 A1 | 12/2011 | Han |
| 2012/0016374 A1 | 1/2012 | Han |
| 2012/0016375 A1 | 1/2012 | Peterson et al. |
| 2012/0022547 A1 | 1/2012 | Hildebrand et al. |
| 2012/0022548 A1 | 1/2012 | Zacharias |
| 2012/0071888 A1 | 3/2012 | Putallaz et al. |
| 2012/0130390 A1 | 5/2012 | Davies et al. |
| 2012/0158007 A1 | 6/2012 | Brown et al. |
| 2012/0165824 A1 | 6/2012 | Tsai |
| 2012/0245591 A1 | 9/2012 | Matthews |
| 2012/0253356 A1 | 10/2012 | Niwa et al. |
| 2012/0289969 A1 | 11/2012 | Seyboth et al. |
| 2012/0289970 A1 | 11/2012 | Pynson |
| 2012/0296264 A1 | 11/2012 | Boukhny et al. |
| 2013/0012956 A1 | 1/2013 | Mirlay |
| 2013/0035939 A1 | 2/2013 | Gilbert et al. |
| 2013/0041382 A1 | 2/2013 | Ben Nun |
| 2013/0197531 A1 | 8/2013 | Boukhny et al. |
| 2013/0197532 A1 | 8/2013 | Boukhny et al. |
| 2013/0281927 A1 | 10/2013 | Jennings et al. |
| 2014/0200590 A1 | 7/2014 | Chen |
| 2015/0088149 A1 * | 3/2015 | Auld ............... A61F 2/1678 606/107 |

(56) References Cited

U.S. PATENT DOCUMENTS

2015/0342726 A1* 12/2015 Deacon .................. A61F 2/148
                                                                         623/6.12

FOREIGN PATENT DOCUMENTS

| | | |
|---|---|---|
| EP | 0477466 A1 | 4/1992 |
| EP | 0937466 A2 | 8/1999 |
| EP | 1481652 B1 | 11/2006 |
| EP | 1175187 A2 | 6/2007 |
| EP | 1857075 A1 | 11/2007 |
| EP | 1736118 A1 | 12/2008 |
| EP | 2368526 A1 | 9/2011 |
| EP | 1344503 B1 | 10/2011 |
| EP | 2324797 A3 | 2/2012 |
| EP | 2074962 B1 | 3/2012 |
| EP | 1539065 B1 | 12/2012 |
| EP | 1748811 B1 | 12/2012 |
| EP | 2178464 B1 | 8/2013 |
| EP | 2491902 B1 | 7/2015 |
| EP | 2560578 B1 | 6/2016 |
| EP | 2502603 B1 | 10/2016 |
| EP | 3075353 A1 | 10/2016 |
| EP | 3122286 | 2/2017 |
| JP | 3207374 | 9/1991 |
| JP | 2004261263 | 9/2004 |
| JP | 2007215990 | 8/2007 |
| JP | 2008500876 | 1/2008 |
| JP | 2016049321 A | 4/2016 |
| RU | 2386423 C2 | 4/2010 |
| WO | 1996037152 A1 | 11/1996 |
| WO | 200164147 A1 | 9/2001 |
| WO | WO 2007-0098622 | 9/2007 |
| WO | WO 2007-0112130 | 10/2007 |
| WO | WO 2010-0028873 | 3/2010 |
| WO | 2011133823 A1 | 10/2011 |
| WO | 2012006616 A2 | 1/2012 |
| WO | 2012086797 A1 | 6/2012 |
| WO | 2013076067 A1 | 5/2013 |
| WO | 2013086612 A1 | 6/2013 |
| WO | 2013184727 A4 | 2/2014 |
| WO | 2014149459 A1 | 9/2014 |
| WO | 2015144870 A1 | 10/2015 |
| WO | 2015144890 A1 | 10/2015 |
| WO | 2015154049 A1 | 10/2015 |
| WO | 2014089250 A1 | 6/2016 |
| WO | 2016208725 A1 | 12/2016 |
| WO | 201747715 A1 | 3/2017 |

OTHER PUBLICATIONS

EP0477466, dated Apr. 1, 1992, Adatomed Pharmazeutische, English Abstract.
RU2386423 with English translation.

* cited by examiner

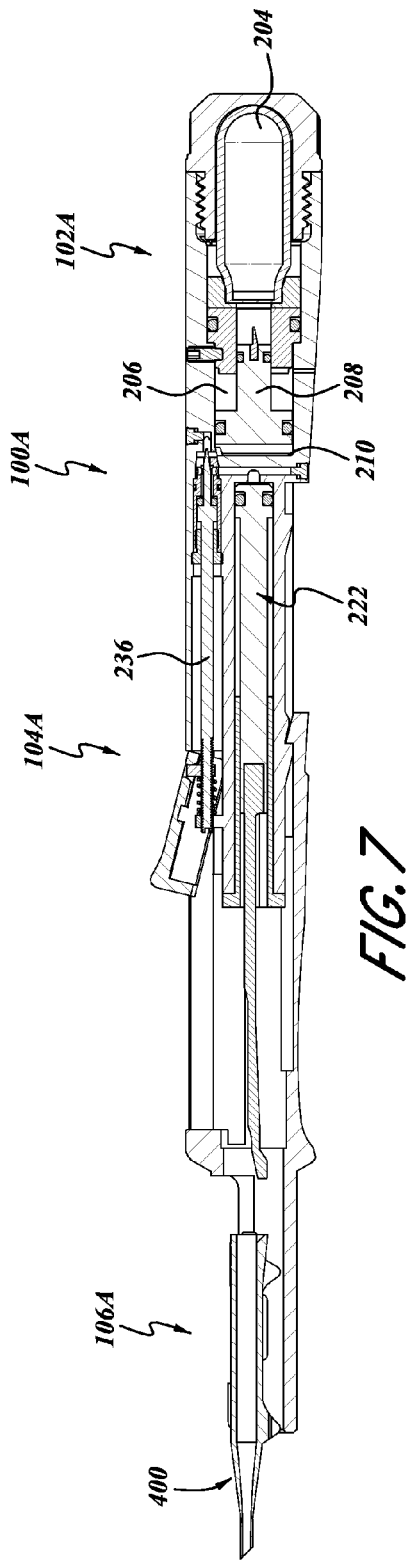
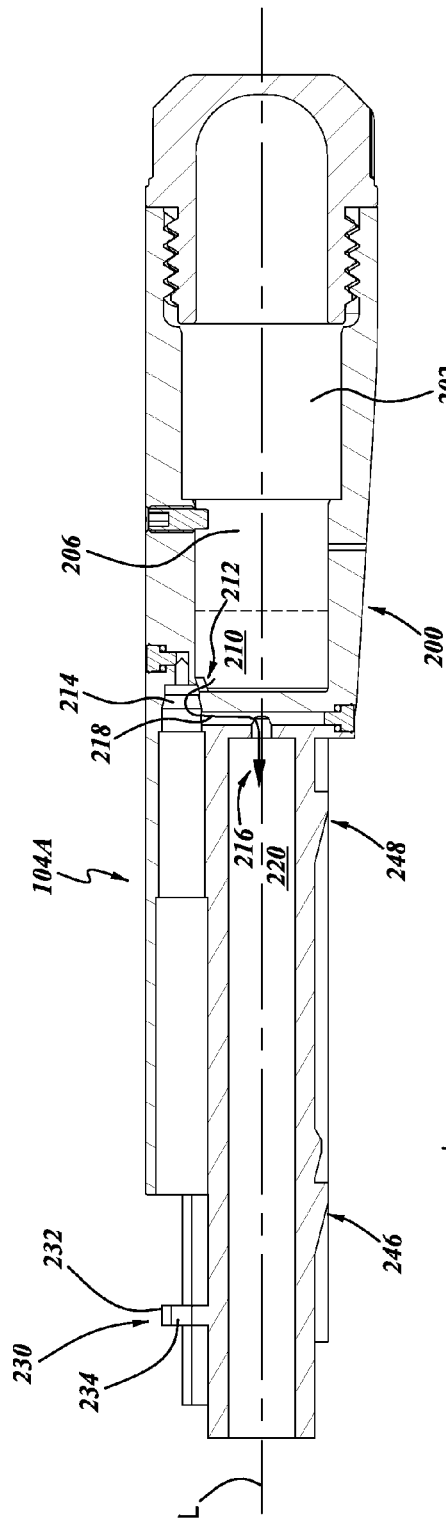
FIG. 7
FIG. 8

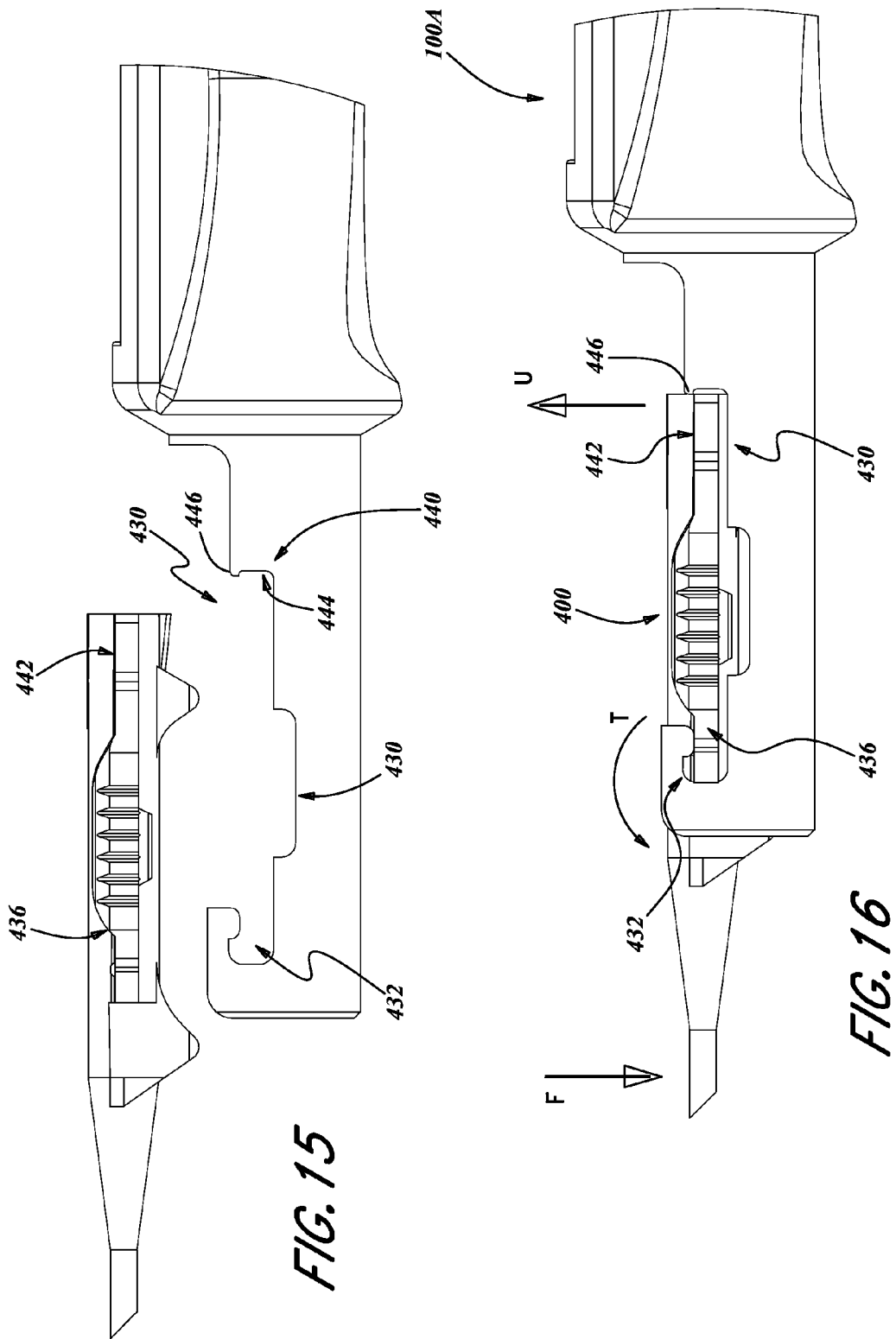

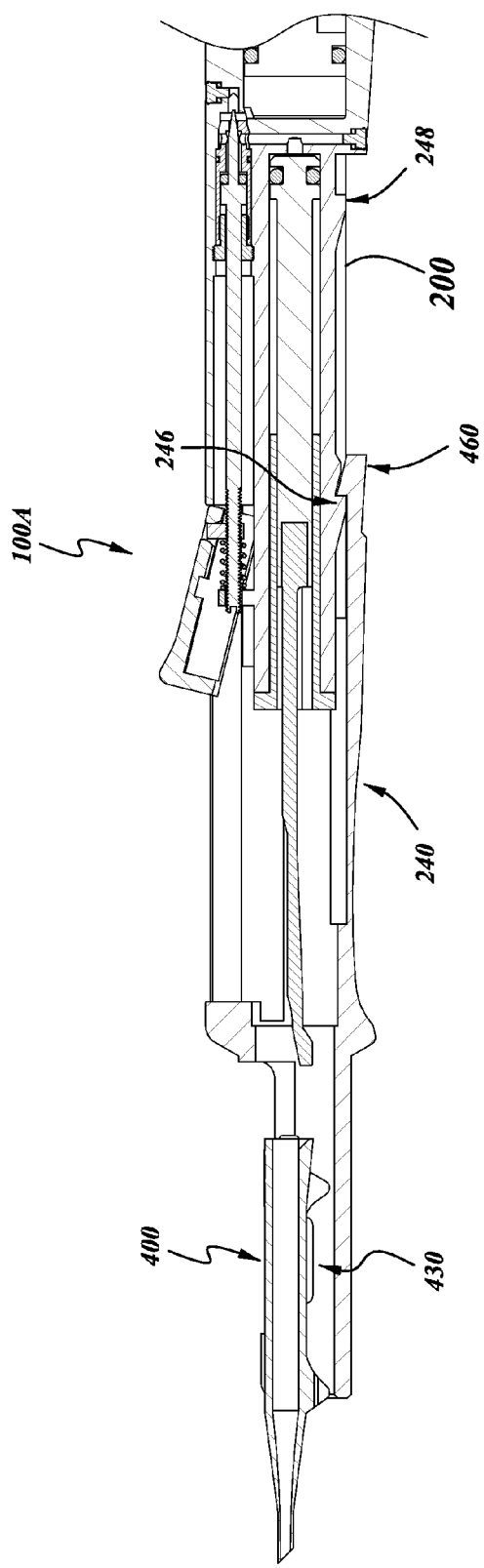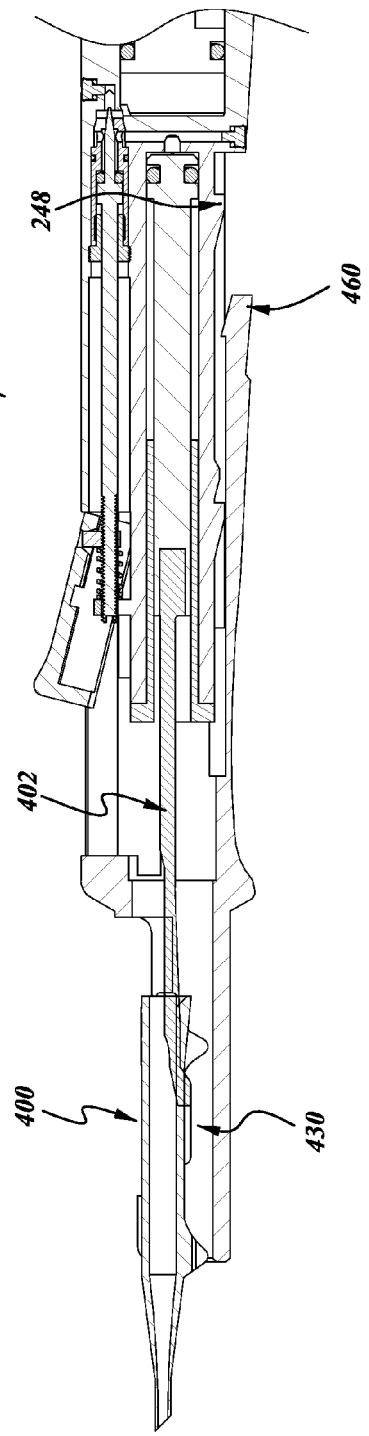

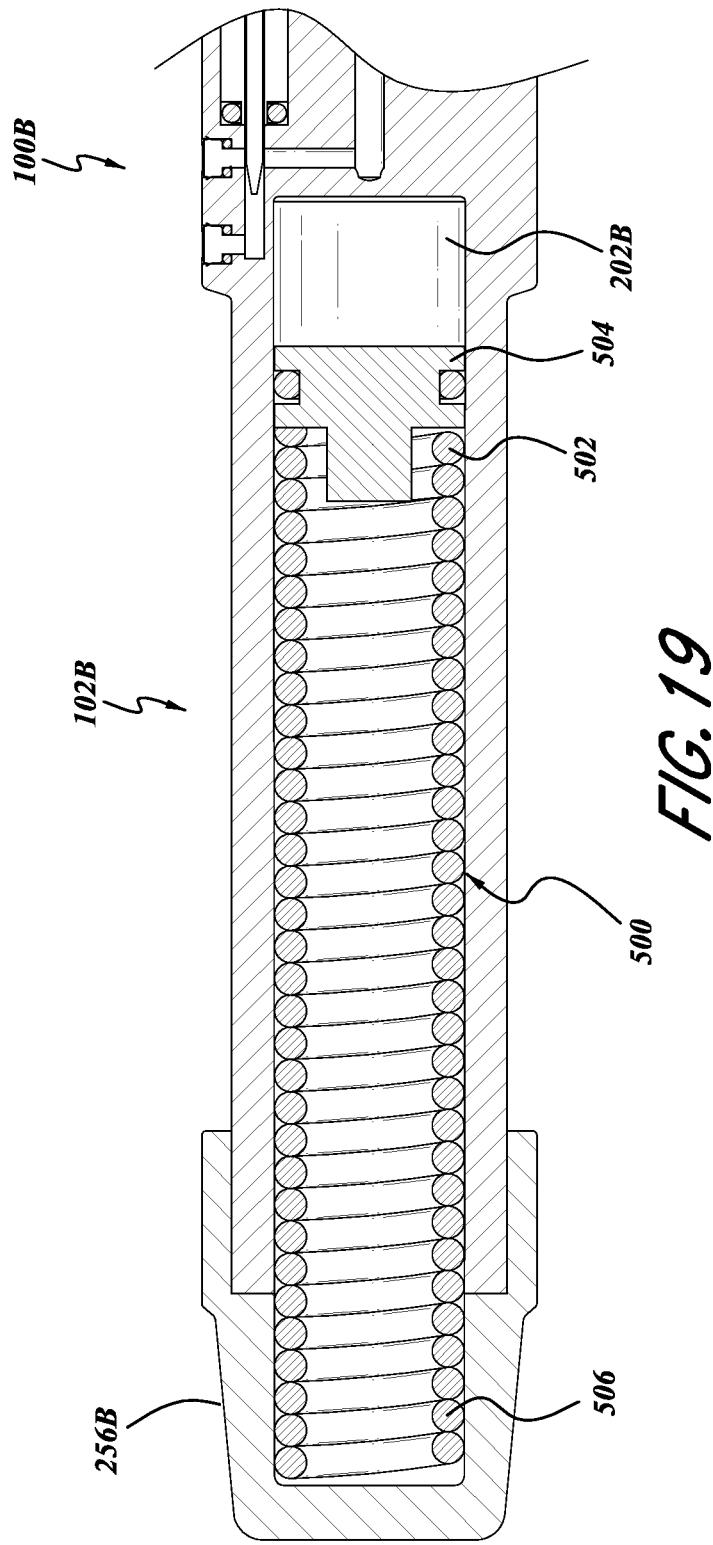

INTRAOCULAR LENS INSERTER

RELATED APPLICATIONS

Any and all applications for which a foreign or domestic priority claim is identified in the Application Data Sheet as filed with the present application are hereby incorporated by reference under 37 CFR 1.57.

The present application is a continuation of U.S. application Ser. No. 14/291,743, filed May 30, 2014, which is a continuation of International Application No. PCT/US2013/044183, filed Jun. 4, 2013, titled INTRAOCULAR LENS INSERTER and published as WO 2013/0184727, which claims priority to U.S. Provisional Patent Application No. 61/655,255, filed Jun. 4, 2012, the entire contents of both of which are hereby incorporated by reference.

TECHNICAL FIELD

The inventions disclosed herein generally relate to devices and methods for inserting intraocular lens into an eye of an animal.

BACKGROUND

A cataract is a clouding that develops in the crystalline lens of the eye or in its envelope (lens capsule), varying in degree from slight to complete opacity and obstructing the passage of light. Early in the development of age-related cataract, the power of the lens may be increased, causing near-sightedness (myopia), and the gradual yellowing and opacification of the lens may reduce the perception of blue colors. Cataracts typically progress slowly to cause vision loss, and are potentially blinding if untreated. The condition usually affects both eyes, but almost always one eye is affected earlier than the other. The following is a list of different types of cataracts:

Senile cataract—Characterized by an initial opacity in the lens, subsequent swelling of the lens, and final shrinkage with complete loss of transparency occurring in the elderly.

Morgagnian cataract—Liquefied cataract cortex forming a milky white fluid, which can cause severe inflammation if the lens capsule ruptures and leaks, occurring as a progression of the cataract. Untreated, the advanced cataract can cause phacomorphic glaucoma. Very advanced cataracts with weak zonules are liable to dislocation anteriorly or posteriorly.

Cataract resulting from trauma—A cataract resulting from trauma to the eye in an otherwise healthy individual. Blunt trauma or penetrating trauma resulting from accidental injury to the eye can result in crystalline lens opacification. Retinal surgery involving a para plana vitrectomy will result in a post-operative cataract in six to nine months after the surgery. Infrequently, an adverse event can occur where by the otherwise healthy crystalline lens is touched by a surgical instrument during Retinal surgery. The crystalline lens clouds and a cataract forms within minutes of the contact.

Congenital cataract—A cataract developed in a child before or just after birth.

In the United States, age-related lenticular changes have been reported in 42% of those between the ages of 52 and 64, 60% of those between the ages 65 and 74, and 91% of those between the ages of 75 and 85.

Age-related cataract is responsible for 48% of world blindness, which represents about 18 million people, according to the World Health Organization. Continued population growth with the shift of the average age will result in increased numbers of patients with cataracts. The increase in ultraviolet radiation resulting from depletion of the ozone layer is expected to further increase the incidence of cataracts.

In many countries, surgical services are inadequate, and cataracts remain the leading cause of blindness. Cataracts are a large cause of low vision in both developed and developing countries. Even where surgical services are available, low vision associated with cataracts can remain prevalent, as a result of long waits for operations and barriers to surgical uptake, such as cost, lack of information and patient transportation problems.

Several factors can promote the formation of cataracts, including long-term exposure to ultraviolet light, exposure to ionizing radiation, secondary effects of diseases such as diabetes, hypertension and advanced age, or trauma (possibly much earlier); they are usually a result of denaturation of lens protein. Genetic factors are often a cause of congenital cataracts, and positive family history may also play a role in predisposing someone to cataracts at an earlier age, a phenomenon of "anticipation" in presenile cataracts. Cataracts may also be produced by eye injury or physical trauma.

A study among Icelandair pilots showed commercial airline pilots are three times more likely to develop cataracts than people with nonflying jobs. This is thought to be caused by excessive exposure at high altitudes to radiation coming from outer space, which becomes attenuated by atmospheric absorption at ground level. Supporting this theory is the report that 33 of the 36 Apollo astronauts involved in the nine Apollo missions to leave Earth orbit have developed early stage cataracts that have been shown to be caused by exposure to cosmic rays during their trips. At least 39 former astronauts have developed cataracts, of whom 36 were involved in high-radiation missions such as the Apollo missions.

Cataracts are also unusually common in persons exposed to infrared radiation, such as glassblowers, who suffer from exfoliation syndrome. Exposure to microwave radiation can cause cataracts. Atopic or allergic conditions are also known to quicken the progression of cataracts, especially in children. Cataracts can also be caused by iodine deficiency. Cataracts may be partial or complete, stationary or progressive, or hard or soft. Some drugs can induce cataract development, such as corticosteroids and the antipsychotic drug quetiapine (sold as Seroquel, Ketipinor, or Quepin).

The operation to remove cataracts can be performed at any stage of their development. There is no longer a reason to wait until a cataract is "ripe" before removing it. However, since all surgery involve some level of risk, it is usually worth waiting until there is some change in vision before removing the cataract.

The most effective and common treatment is to make an incision (capsulotomy) into the capsule of the cloudy lens to surgically remove it. Two types of eye surgery can be used to remove cataracts: extra-capsular cataract extraction (ECCE) and intra-capsular cataract extraction (ICCE). ECCE surgery consists of removing the lens, but leaving the majority of the lens capsule intact. High frequency sound waves (phacoemulsification) are sometimes used to break up the lens before extraction. ICCE surgery involves removing the lens and lens capsule, but it is rarely performed in modern practice. In either extra-capsular surgery or intra-capsular surgery, the cataractous lens is removed and replaced with an intraocular plastic lens (an intraocular lens implant) which stays in the eye permanently. The intraocular lens is placed into a cartridge and inserted through the small surgical incision. The inserter folds the intraocular lens and pushed it through a small needle. The end of the needle is positioned within the capsular bag. When the folded intraocular lens exits the end of the needle, it slowly unfolds as the surgeon manipulated the lens into its final position. Cataract operations are usually performed using a local anesthetic, and the patient is allowed to go home the same day. Until the early twenty-first century intraocular lenses were always monofocal; since then improvements in intraocular technology allow implanting a multifocal lens to create a visual environment in which patients are less dependent on glasses. Such multifocal lenses are mechanically flexible and can be controlled using the eye muscles used to control the natural lens.

Complications are possible after cataract surgery, including endophthalmitis, posterior capsular opacification and retinal detachment.

Laser surgery involves cutting away a small circle-shaped area of the lens capsule, enough to allow light to pass directly through the eye to the retina. There are, as always, some risks, but serious side effects are very rare. As of 2012 research into the use of extremely-short-pulse (femtosecond) lasers for cataract surgery was being carried out. High frequency ultrasound is currently the most common means to extract the cataract lens.

Cataract surgeries are conducted in an operating room under sterile conditions to prevent the risk of infection, particularly endophthalmitis; a rapid devastating infection that can cause blindness in a few days. The patient's eye is cleaned with an antiseptic, and then isolated with a sterile drape that fully covers the patient with only the eye exposed. A sterile field is established around the patient such that any personnel or instrumentation must be suitably scrubbed, draped or sterilized following standard aseptic procedures.

With reference to FIGS. 1 and 2, such a prior art type of cataract surgery includes using a surgical microscope to view the interior of the eye through a patient's cornea and iris. The surgeon typically makes two incisions 10, 12 in the patient's cornea, close to the limbus, to enable surgical instruments to gain access to the interior segment of the eye and to implant an intraocular lens after the cataract crystalline lens has been removed. For example, an intraocular lens inserter 14 can be inserted through the incision 10 and a positioning device 16 can be inserted through the incision 12.

The surgery typically includes creating a full-circle tear in the center of the capsular bag on the interior side, called a "capsulorhexis," and remove the torn circle of the capsule. Then, the cataract crystalline lens is removed using a phacoemulsifer, an ultrasonic infusing and aspirating instrument that breaks up the cataract and aspirates the fragments, removing the cataract.

The lingering cortical material that is attached to the inner surface of the capsular bag is then aspirated using an infusion/aspirating instrument. The intraocular lens 18 is then inserted using the lens inserter 14 and positioned within the capsular bag using the positioning device 16 or other devices.

The lens inserter 14 transfers the flat intraocular lens 18 through the small clear corneal incision 10 into the capsular opening (capsulorhexis) and to its final position within the capsular bag. The inserter 14 pushes the flat lens 18 through a cartridge which causes the lens to fold and pass through a tubular portion of the cartridge which is placed onto the small incision 10. As the lens 18 emerges out of the tubular end of the cartridge 14, it slowly unfolds and returns to its original flat shape.

Recent advances in femtosecond laser instrumentation has automated the process of making entry incisions and the capsulorhexis as well as pre-cutting the cataract making the cataract surgical procedure more precise, safer, and easier for the surgeon to execute.

The majority of current lens inserters are manually operated re-usable instruments with primarily one of two means to push the lens: a lead screw or plunger. The lead screw approach provides consistent and smooth delivery of the lens, however slowly, and requires the surgeon or an assistant to turn the manual lead screw as the surgeon positions the tip of the instrument The plunger approach does not require an assistant, as the surgeon uses their thumb to drive the lens forward, much like injecting a drug from a syringe. Additionally, the surgeon can more readily control the speed of delivery, swiftly moving though the less critical portions and slowing for the more delicate segments. A draw back of the plunger approach can emerge when the lens becomes stuck resulting in a more forceful push by the surgeon where upon clearance of the hang-up, the lens can over-shoot its exit and injure the patient.

Re-usable instrumentation requires re-processing (cleaning and sterilization) resulting in additional instrumentation overhead and increased risk of Toxic Anterior Segment Syndrome (TASS) http://www.cdc.gov/mmwr/preview/mmwrhtml/mm5625a2.htm.

Recently, efforts have been made to perform such lens replacement surgeries using smaller corneal incisions. For example, as shown schematically in the illustration of FIG. 3, typically, the distal end of an intraocular lens inserter 14 is inserted completely through the incision 10, during a procedure of inserting an intraocular lens 18.

However, with reference to FIG. 4, recently surgeons have been adopting a "wound-assist" technique, wherein only a small portion of the tip 20 of the intraocular lens inserter 14 is inserted into the incision 10, wherein the incision 10 is smaller than the incisions previously made, such as during the procedure illustrated in FIG. 3. As such, the intraocular lens 18, in its folded state, is pushed through and slides along interior surfaces of the incision 10. This allows the incision 10 to be smaller and the wound itself (incision 10) becomes a lumen for inserting the lens 18 into the eye.

During such a procedure, the surgeon can use the distal end 20 of the tip of the intraocular inserter 14 to help hold the incision 10 open. For example, the surgeon might apply a lateral force in the direction of arrow 22 in order to hold the incision 10 open such that the lens 18 can be pushed therethrough.

SUMMARY OF THE INVENTION

An aspect of at least one of the inventions disclosed herein includes the realization that an intraocular lens inserter design can allow a surgeon to actuate and thus discharge a lens from an inserter device with one hand can provide a surgeon and can also reduce the manual force that must be applied by the surgeon. For example, in some known conventional devices, such as plunger devices, a surgeon must use significant manual force against the proximal end of the plunger to push the lens through the end of the inserter device. This makes it more difficult for the surgeon to hold the device in the desired orientation and location during insertion. This problem is more significant in the surgical procedures more recently adopted such as that described above with reference to FIG. 4. Thus, an intraocular lens insertion device that provides assisted discharge force can help a surgeon perform the surgical procedure as desired.

Another aspect of at least one of the inventions disclosed herein includes the realization that significant costs for such devices can be reduced by the use of an inserted device having an incorporated mechanism for storing energy for providing a discharge force, which is not connected by a tether, for example, to a separate console. For example, some known types of surgical devices include electrical motors or pneumatic systems that are operated by standalone consoles that provide either electrical power to an electric motor or compressed air to a compressed air motor inside a handpiece of a surgical device. Such systems require the surgeons to purchase or rent the console devices for use with such specialized surgical tools.

Thus, by providing an intraocular lens inserter with energy storage for providing a discharge force, the intraocular lens inserter is more portable and avoids the requirement for a surgeon to purchase or rent a separate standalone console.

Another aspect of at least one of the inventions disclosed herein includes the realization that compressible energy storage devices, such as springs, or compressed air, can provide convenient and portable means for storage of energy which can be output as forces. However, such energy storage devices are more difficult to control for providing, for example, constant velocity output. Thus, an aspect of at least one of the inventions disclosed herein includes the realization that providing an actuating circuit operating with a substantially incompressible fluid, such as a liquid, accommodates the use of mechanisms that can provide more fine control over the velocity of downstream components, even where energy is supplied by a compressible storage device, such as springs or compressed air.

Another aspect of at least one of the inventions disclosed herein includes the realization that a hand-held intraocular lens inserter can be made with an incorporated energy storage device and a movement control actuator, with sufficient simplicity that the resulting device can be designed as a single use device and thus disposable, thereby avoiding the costs of resterilization and the potential for cross-contamination. Thus, for example, an intraocular lens inserter device can include a compressible energy storage device and an actuator configured to operate with a substantially incompressible fluid for controlling the release of the energy stored by the energy storage device and the movement of downstream components, such as a lens insertion rod.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the Detailed Description and claims when considered in conjunction with the following figures, wherein like reference numerals refer to similar elements throughout the figures.

FIG. 7 is a side elevational and cross-sectional view of the intraocular lens inserter of FIG. 6.

FIG. 8 is a side elevational and cross-sectional view of a portion of a housing member of the intraocular lens inserter of FIG. 7.

FIG. 15 is an enlarged side elevational view of a lens cartridge removed from the lens cartridge holding portion.

FIG. 16 is a view of the inserter of FIG. 15 with the lens cartridge inserted into the lens cartridge holder portion.

FIG. 17 is a partial cross-sectional view of the inserter of FIG. 16 prior to the lens cartridge being engaged with a plunger.

FIG. 18 is a cross-sectional view of the inserter shown after the lens holder portion has been moved axially to engage the plunger with the lens cartridge.

FIG. 19 is an illustration of a further embodiment of the inserter in FIG. 6, in which the energy storage device is in the form of a spring.

DETAILED DESCRIPTION OF THE PREFERRED EMBODIMENT

Figure 1:
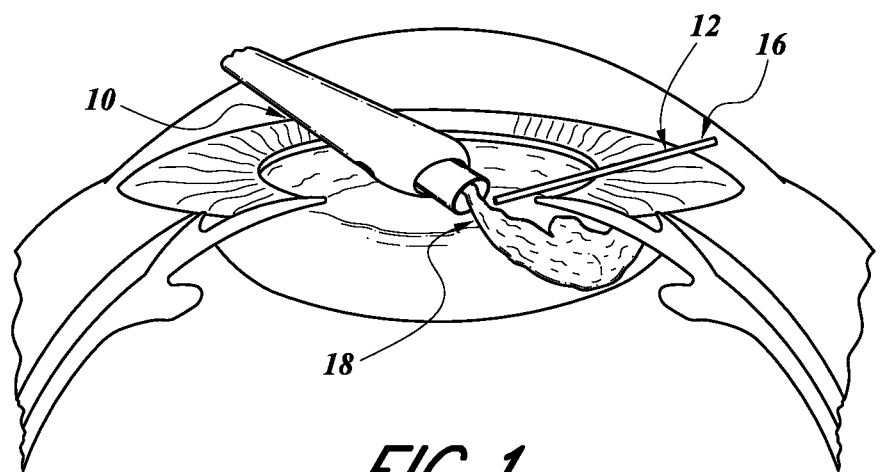
FIG. 1 is an enlarged sectional view of a human eye with an intraocular lens inserter inserted through an incision in the cornea and a positioning device inserted through a second incision, with an intraocular replacement lens shown as being partially ejected from the intraocular lens inserter.
Figure 2:
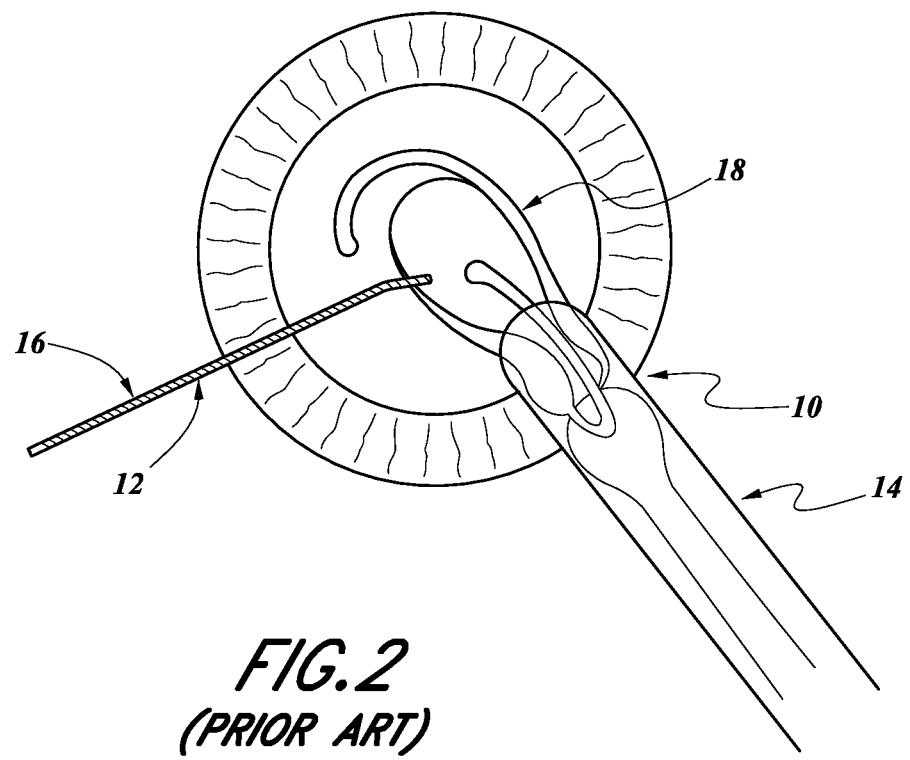
FIG. 2 is a front plan view of the procedure illustrated in FIG. 1.
Figure 3:
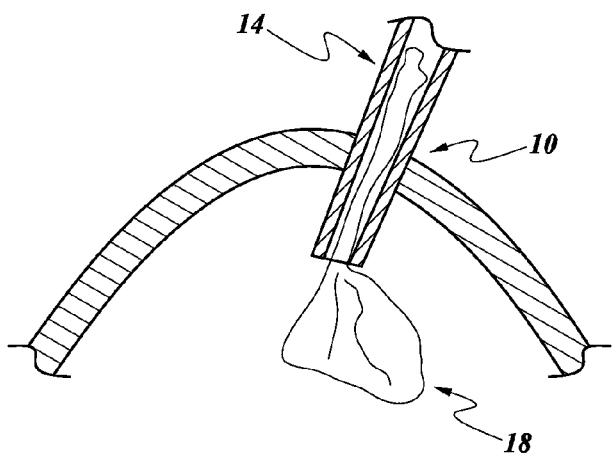
FIG. 3 is a schematic diagram of a portion of the arrangement shown in FIG. 1, with the distal tip of an intraocular lens inserter inserted completely through an incision and discharging a replacement lens.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the proceeding technical field, background, brief summary, or the following detailed description.

Certain terminology may be used in the following description for the purpose of reference only, and thus are not intended to be limiting. For example, terms such as "upper", "lower", "above", and "below" refer to directions in the drawings to which reference is made. Terms such as "proximal", "distal", "front", "back", "rear", and "side" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The inventions disclosed herein are described in the context of intraocular lens inserters for the treatment of cataracts. However, the inventions disclosed herein can be used in other context as well with regard to surgical devices that are required to discharge devices, for example, into or beyond the tissues of an animal, such as a human.

Figure 5:
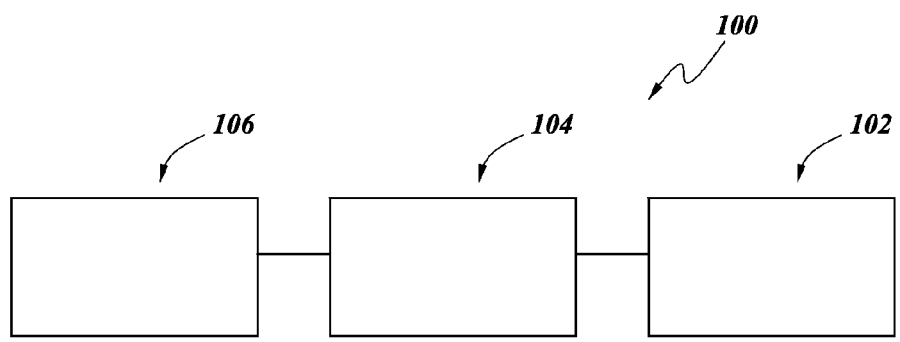
FIG. 5 is a schematic illustration of an embodiment of an intraocular lens inserter.

With reference to FIG. 5, an intraocular lens inserter 100 can include an energy storage device 102, an actuator device 104, and a lens discharge portion 106. The energy storage portion 102 can be in the form of any type of energy storage device. In some embodiments, the energy storage portion 102 is in the form of a device for storing a compressible fluid, mechanical springs, or other compressible types of energy storage devices. Other types of energy storage devices can also be used.

In some embodiments, the energy storage portion 102 can be configured to discharge mechanical energy from the energy stored therein. For example, where the energy storage device 102 is in the form of a compressed gas container, the energy storage device 102 can discharge such compressed gas which therefore provides an output of mechanical energy. Similarly, where the storage device 102 is in the form of a mechanical spring, such a spring can output linear or torsional movement, which is also a form of mechanical energy.

The actuator portion 104 can be any type of actuator configured to provide controllable actuation of the output of mechanical energy from the energy storage portion 102. For example, in some embodiments, the actuator portion 104 can be in the form of a mechanical or electronic button or lever for providing a user with means for controlling the output of mechanical energy from the energy storage portion 102. For example, the actuator 104 can be in the form of a button or other electronic devices configured to provide variable resistance or movement associated with a mechanical member used for outputting the energy from the energy storage portion 102. The actuator portion 104 can also provide for the control of an output member configured for interaction with the intraocular lens portion 106. For example, the actuator portion 104 can include an output plunger or other device for interacting with the intraocular lens portion.

The intraocular lens portion 106 can be configured to interact with or retain an intraocular lens cartridge which is widely commercially available from several different sources. For example, the intraocular lens portion 106 can be configured to releasably engage with an intraocular lens cartridge commercially available as a Monarch available from Alcon. The intraocular lens portion 106 can also be configured to move between an open position configured for allowing an intraocular lens cartridge to be engaged with the lens portion 106 and a closed portion in which the lens portion 106 engages with the lens cartridge.

As such, in operation, the actuator portion 104 can be manipulated by a user, such as a surgeon, to control the output of mechanical energy from the energy storage portion 102, to thereby control the discharge of a lens from a lens cartridge retained by the lens portion 106. Further, the inserter 100 can be configured to be hand-held, and in some embodiments, disposable.

With reference to FIGS. 6-18, a further embodiment of the lens inserter 100 is illustrated there and identified by the reference number 100A. The features and components of the lens inserter 100A that can be the same or similar to corresponding components of the lens inserter 100 have been identified with the same reference numeral, except that the letter "A" has been added thereto.

Figure 6:
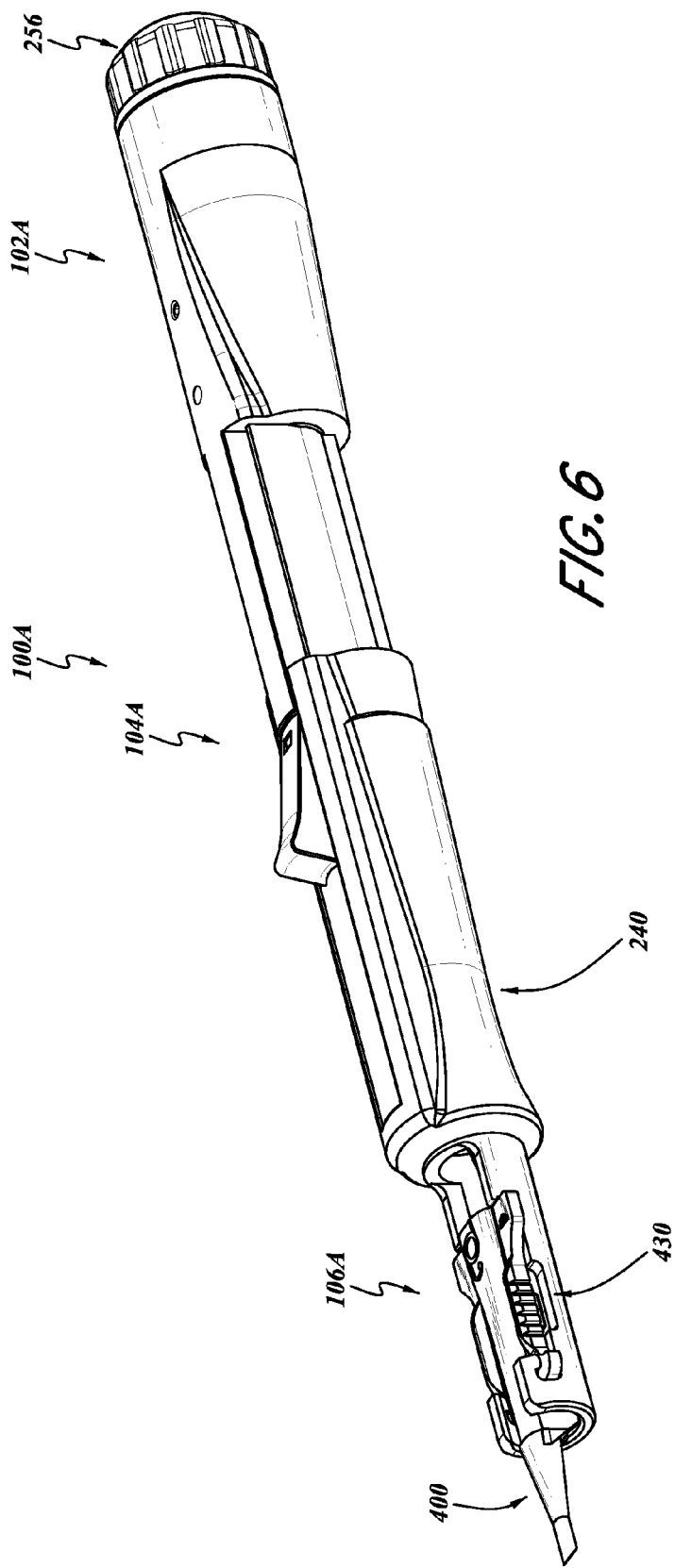
FIG. 6 is a perspective view of a further embodiment of an intraocular lens inserter.

With reference to FIGS. 6-8, the intraocular lens inserter 100A also includes an energy storage portion 102A, an actuator portion 104A, and a lens portion 106A.

In the illustrated embodiment, with reference to FIG. 8, the inserter 100A includes a main body portion 200 which includes various cavities, recesses, and conduits, and, in the present embodiment, provides for communication between the energy storage portion 102A and the actuator portion 104A. FIG. 8 illustrates the body portion 200 with all other components removed therefrom. In some embodiments, optionally, the body portion 200 can be made from a single piece of material forming a monolithic body. However, other configurations can also be used.

In some embodiments, the body portion 200 includes an energy storage receiving portion 202. In some embodiments, the receiving portion 202 is configured as a recess within the body 200, sized and configured to receive a container of compressed gas. In some embodiments, the recess 202 can be sized to receive a canister of compressed carbon dioxide 204. Such containers of compressed gas and, in particular, carbon dioxide, are widely commercially available.

The housing 200 can also include a piston chamber 206 configured to receive gas discharged from the container 204. The piston chamber 206 can include devices for interacting with the gas from the container 204 for providing usable mechanical energy. For example, as shown in FIG. 7, a piston 208 can be disposed in the piston chamber portion 206. In some embodiments, the piston 208 subdivides the piston chamber portion 206 into a gas-receiving portion and a liquid-receiving portion 210.

The housing 200 can also include a conduit 212 connecting the energy storage portion 102A with the actuator portion 104A. For example, the conduit 212 can provide a flow path between the liquid receiving portion 210, along the direction of arrow 216, into the actuator portion 104A.

The conduit 212 can include an aperture in a portion of the liquid-receiving portion 210, that leads into an actuator control portion 214, then to a lateral connector portion 218, into a further liquid-receiving portion 220 of the actuator portion 104A.

The actuator receiving portion 214 can be configured to receive an actuator for controlling the flow of fluid along the conduit 212. Additionally, the chamber 220 can be configured to receive a piston 222, described in greater detail below.

With continued reference to FIG. 8, the body 200 can also include an actuator mounting portion 230. The actuator mounting portion 230 can be in the form of a projection 232 extending radially outwardly from the longitudinal axis L of the body 200. The projection 232 can include an aperture 234 and could be configured to receive an actuator rod 236 (FIG. 7).

The body 200 can also include various other outer surfaces and devices for engagement with a sliding cartridge engagement member 240 (FIG. 6), described in greater detail below. For example, the outer surface 242 of the actuator portion 104A of the body 200 can include various engagement devices 246, 248, and/or other ridges for providing alignment and engagement with the engagement device 240. Such features are described in greater detail below with reference to FIG. 14.

Figure 9:
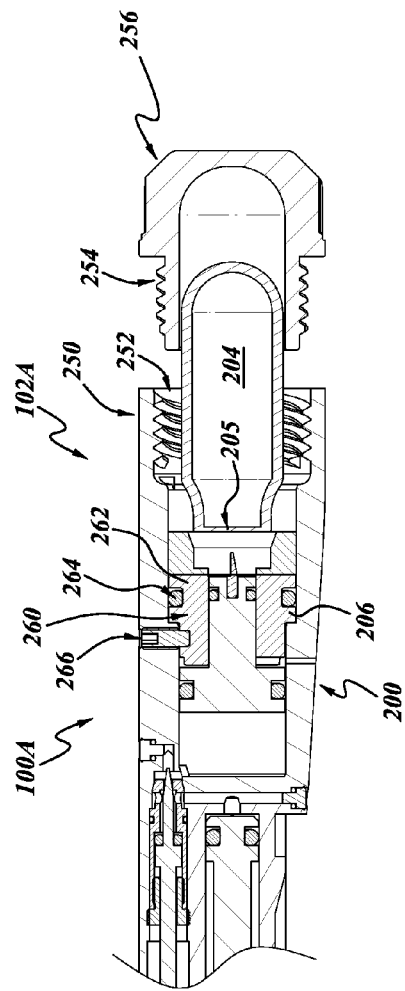
FIG. 9 is an enlarged sectional view of an energy storage portion of the lens inserter of FIG. 6 and in a partially exploded view.
Figure 10:
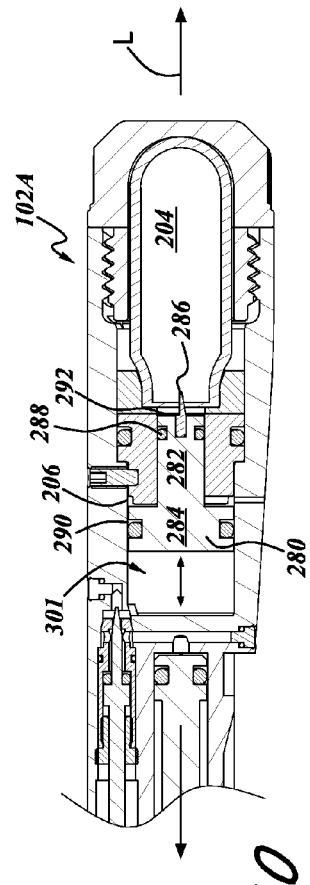
FIG. 10 is also a cross-sectional view of lens inserter of FIG. 6 showing an energy storage device being pierced by a piercing device and within end caps screwed down over the energy storage device.
Figure 11:
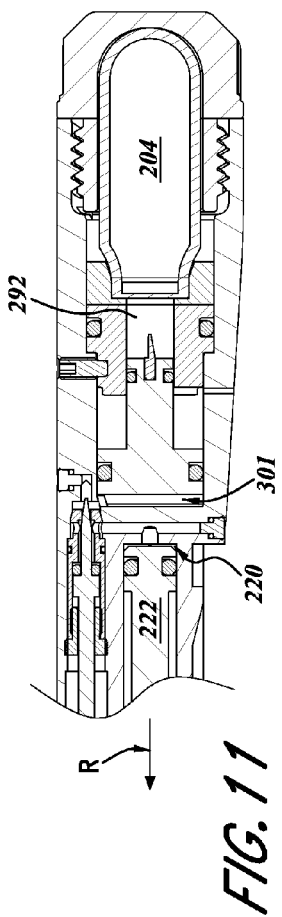
FIG. 11 is a cross-sectional view of the inserter of FIG. 6 showing movement of a piston after an expanding gas has been discharged from the energy storage device.

With reference to FIGS. 9-11, the storage portion 102A is illustrated in further detail, including various components that can be included within the body member 200. The distal end 250 of the body member 200 can include internal threads 252 configured for engagement with external threads 254 disposed on a removable end cap 256.

Additionally, the energy storage portion 102A can include a bulkhead member 260. The bulkhead member 260 can be configured to provide for secure engagement with a chosen energy storage device used with the energy storage portion 102a. As noted above, the illustrated embodiment is designed for use with a cartridge of compressed carbon dioxide 204. Thus, in the illustrated embodiment, the bulkhead member 260 includes an upstream end 262 configured for abutting engagement with a distal end 205 of the cartridge 204. The bulkhead member 260 can also include a sealing device, such as an O-ring 264, for providing a sealing engagement with an inner surface of the piston chamber 206. In the illustrated embodiment, the bulkhead member 260 remains stationary during operation. Thus, the inserter 100a also includes a set screw 266 which extends through the body portion 200 for secure engagement with the bulkhead member 260. Other designs can also be used.

The energy storage portion 102A can also include an accumulator piston 280. In the illustrated embodiment, the accumulator piston 280 is slidably engaged with two surfaces. Firstly, the accumulator piston 280 includes a first portion 282 engaged with an inner surface of the bulkhead member 260 and a downstream portion 284 engaged with an inner surface of the piston chamber 206. Additionally, in the illustrated embodiment, the piston 280 includes a piercing needle 286 which is configured to pierce a seal that is commonly used on compressed gas cartridges, such as the carbon dioxide compressed gas cartridge 204.

The piston 280 is configured to move slidably along the longitudinal axis L of the inserter 100A. As such, the piston 280 includes an O-ring 288 for sealing against the inner surface of the bulkhead 260 and a second O-ring 290 for providing a sliding seal with the inner surface of the piston chamber 206.

In some embodiments, the O-ring seal 288 can be configured to maintain all of the gas discharged from the cartridge 204 in the area 292 disposed between the piston 280 and the cartridge 204. Additionally, the piston chamber 206 can be configured to receive a substantially incompressible fluid, such as a liquid, including but not limited to, silicone oil, propylene glycol, glycerin, saline, water, or other substantially incompressible fluids. For purposes of illustration, the piston 280 and the downstream or distal portion of the piston chamber 206 can be considered as a substantially incompressible fluid-receiving chamber 300. Thus, in some embodiments, the O-ring 290 is configured to maintain any liquid or fluid in the chamber 300 in the distal portion of the chamber 206.

During operation, when the cap 256 is screwed into the threads 252, the cartridge 204 is thereby pushed into the piercing needle 286, thereby opening the cartridge 204 and releasing the compressed gas therein into the space between the cartridge 204 and the bulkhead 260 and the distal proximal end portion 282 of the piston 280.

With reference to FIG. 11, when the actuator portion 104A is operated appropriately, the pressurized gas from the cartridge 204 continues to expand into the gas-receiving portion 292, thereby pressurizing any fluid or liquid in the substantially incompressible fluid receiving portion 301. Actuation of the actuator portion 104A allows the pressurized fluid in the chamber 301 to flow outwardly therefrom and into the chamber 220 to thereby drive the piston 222 longitudinally in the direction of arrow R (FIG. 11), described in greater detail below.

Figure 12:
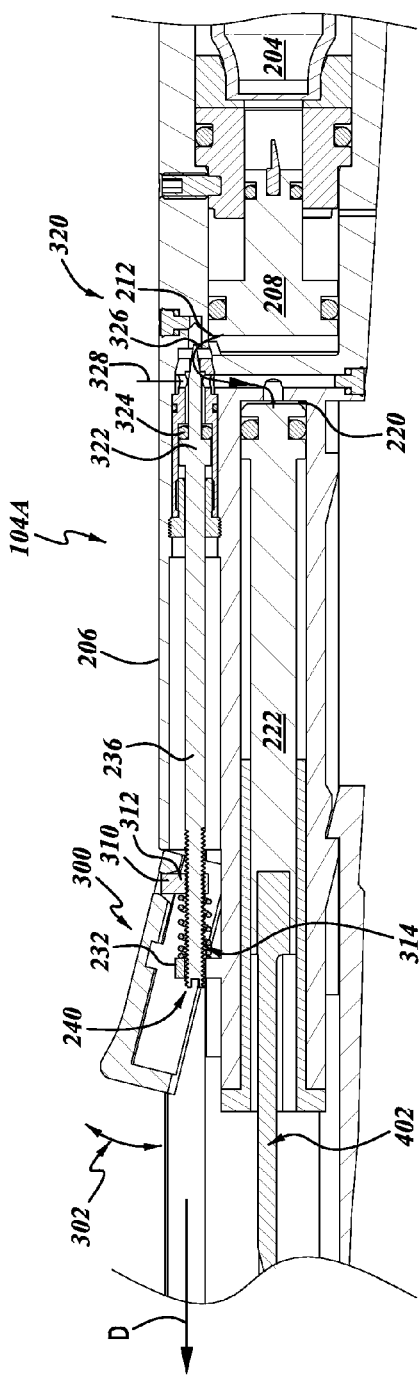
FIG. 12 is an enlarged sectional view of an actuator portion of the inserter of FIG. 6.

With continued reference to FIG. 12, the actuator portion 104A can include an actuator member 300 mounted relative to the housing member 200 so as to be movable between an unactuated position (illustrated in FIG. 12) and an actuated position (not shown). For example, the lever member 300 can be attached to the housing 200 with the hinge member (not shown), such that the actuator member can be pivotable along the arc 302. The actuator member 300 can also be engaged with the rod 236 which can be configured to provide a flow control function for controlling the flow of substantially noncompressible fluid from the chamber 300 toward the chamber 220 for moving the piston 222. For example, the piston rod 236 can include a distal end 240 which extends through the aperture 234 of the projection 232 and a proximal end 320 configured to provide a flow control function.

The distal end 240 of the rod 236 can include a slot for engagement with a screwdriver to provide adjustment of the positioning of the rod 236. For example, the lever member 300 can also include an engagement member 310 pivotally mounted to the lever member 300. The engagement member 310 can include a threaded portion 312 configured for engagement with external threads on the distal portion 240 of the rod 236.

Additionally, a spring 314 can provide a bias of the lever member 300 to the unactuated position. Connected as such, when the lever mover 300 is moved through the arc 302, and more particularly, when the lever member 300 is moved downwardly from the position illustrated in FIG. 12, the engagement member pulls the rod 236 in a distal direction D, thereby moving the flow control portion 320 in the direction of arrow D. The spring 314 provides a bias return action for returning the lever member 300 to the position illustrated in FIG. 12, when released by a user.

With continued reference to FIG. 12, the proximal portion 320 of the rod 236 can include a piston member 322 and seal, in the form of an O-ring 324. The proximal portion 320 can also include a needle portion 326 configured to cooperate with a throat portion 328. Using well known techniques, the engagement and cooperation of the needle portion 326 with the throat portion 328 can be used to control a flow of substantially incompressible fluid along the conduit 212. For example, when the lever 300 is moved downwardly from the position illustrated in FIG. 12, the piston rod is moved distally in the direction D, thereby moving the needle portion 326 also in the direction of arrow D, thereby forming or increasing a gap between the needle portion 326 and the throat portion 328. As such, fluid flows through the conduit 212, for example, a substantially incompressible fluid pressurized by the piston 208 due to interaction with gas discharged from the cartridge 204 can thereby flow through the conduit 212 toward the piston 222.

Figure 13:
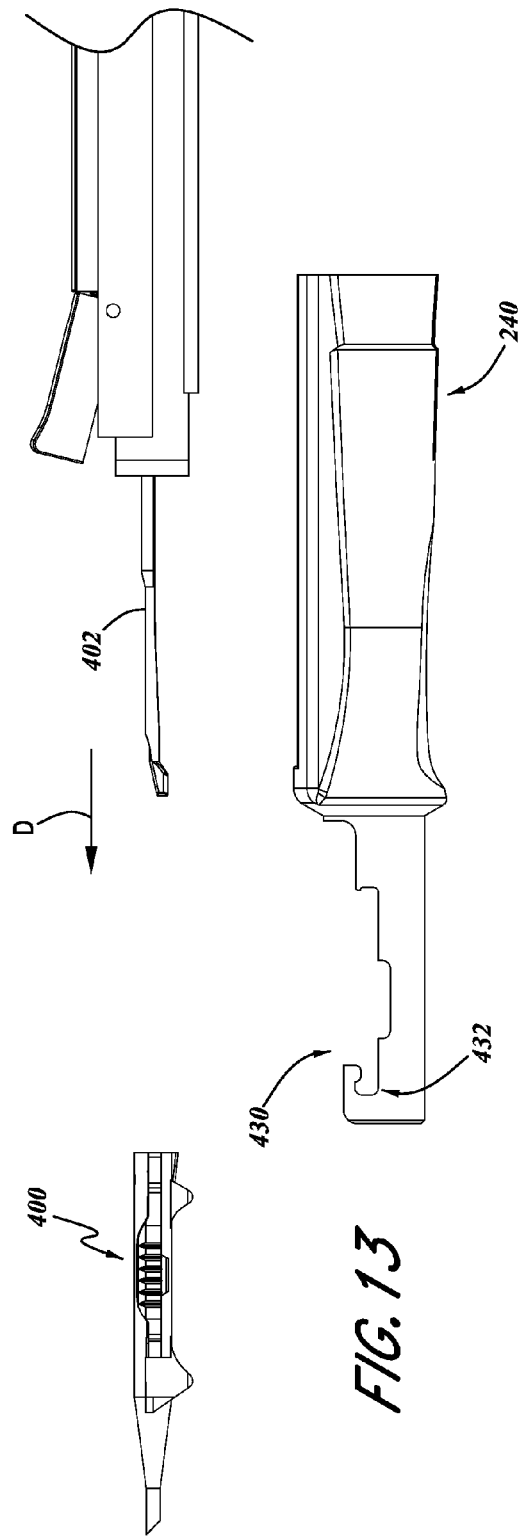
FIG. 13 is an exploded view of a lens cartridge holder portion of the inserter of FIG. 6.

When the substantially incompressible fluid presses against the piston 222, the piston 222 also moves in the direction of arrow D. This movement of the piston 222 can be used to discharge a lens from the cartridge 400. More specifically, as illustrated in FIGS. 12 and 13, a plunger 402 can be attached to a distal end of the piston 222. Thus, as the piston 222 is moved by the flow of fluid through the conduit 212, the plunger 402 is also moved in the direction of arrow D. This movement of the plunger 402 can be used to discharge a lens disposed within the cartridge 400, in a technique that is well known in the art.

Figure 14:
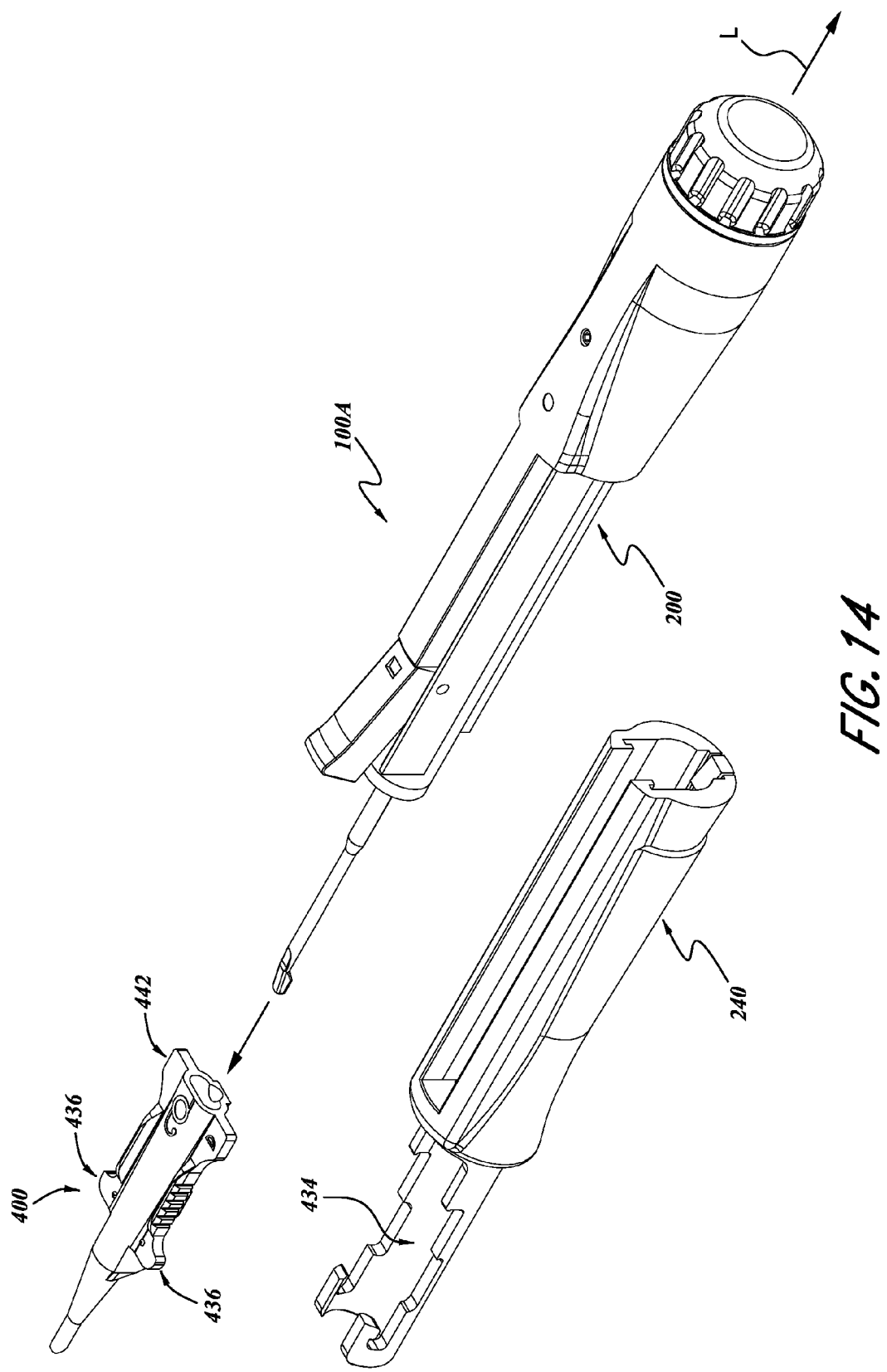
FIG. 14 is an enlarged perspective and exploded view of the inserter shown in FIG. 13.

With reference to FIGS. 13 and 14, the cartridge engagement member 240 can include a cartridge receiving portion 430. For example, the cartridge receiving portion 430 can include a distal wing engagement portion 432 and a body receiving portion 434. The wing receiving portion 432 and the body receiving portion 434 can be sized in accordance with the outer dimensions of commercially available lens cartridges 400, which are well known in the art.

The distal wing receiving portion 432 can include a recess designed to engage the wings 436 of the lens cartridge 400. Thus, when the cartridge 400 is engaged with the cartridge receiving portion 430, as shown in FIG. 6, the cartridge 400 is generally aligned with the plunger 402.

With continued reference to FIGS. 15 and 16, the cartridge receiving portion 430 can optionally include a proximal engaging portion 440 configured to engage with a proximal portion of the cartridge 400. For example, in some commercial embodiments of the cartridge 400, the cartridge 400 includes rearward wings 442 or other rearward surfaces. The cartridge engagement portion 430, therefore, can include an additional proximal recess 444 and an engagement device 446, for a positive engagement with the wings 442. Thus, as shown in FIG. 16, when the cartridge 400 is engaged both with the forward engagement portion 432 and the rearward engagement portion 444, with the projection 446 extending over the rearward wings 442, the cartridge 400 is more securely seated within the cartridge receiving portion 430.

Figure 4:
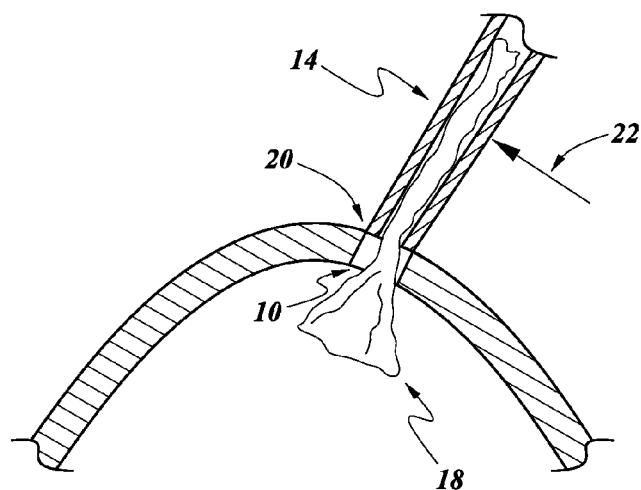
FIG. 4 is a schematic illustration of a different procedure than that illustrated in FIG. 3, in which the distal tip of the intraocular lens inserter is inserted only partially into the incision.

This can provide a substantial benefit to a surgeon using the inserter 100a. For example, with the projection 446 extending over the rearward wing 442, if the surgeon applies a force to the inserter 100a, in the direction of arrow F (FIG. 16), a torque T can be created or imparted onto the cartridge 400, thereby tending to cause the cartridge to pivot about the distal receiving portion 432, which can thereby tend to cause the proximal end of the cartridge 400 to lift upwardly in the direction of arrow U. However, the engagement portion 446 can help retain the proximal portion of the cartridge 400 within the receiving portion 430. This type of force can be created during execution of surgical procedures that are becoming more common, such as that described above with reference to FIG. 4, known as the "wound-assist" technique.

With continued reference to FIGS. 14-18, the member 240 can also be slidably engaged with the body 200. Thus, the member 240 can include various internal surfaces configured to cooperate with outer surfaces of the body 200. Thus, the member 240 can be slid longitudinally along the body 200, parallel to the longitudinal axis L of the inserter 100a.

For example, with reference to FIGS. 17 and 18, the portion 240 can be moved to a distal position, show in FIG. 17. In this position, the lens receiving portion 430 is spaced apart from the plunger 402. As such, the cartridge 400 can be inserted into the cartridge receiving portion 430 without interference of the plunger 402. Thus, after the cartridge is received as such, as shown in FIG. 18, the portion 240 can be slid backwards relative to the body 200 until the plunger 402 engages or presses against a lens within the cartridge 400.

As noted above, the body 200 can include various detents or ramps or other portions 246, 248 which can engage with a portion of the member 240 for providing positive engagement into various positions. For example, the portion 240 can include a ramp and hook portion 460 configured to engage with the portion 246 and portion 248 of the housing member 200. Thus, the member 240 can be positively engaged in the position illustrated in FIG. 17 with the body member 200, and then when pulled in the proximal direction, so as to move the plunger 402 into the cartridge 400, the portion 460 can engage with the proximal portion of the housing 200 to thereby engage into a retracted position. Other designs can also be used to provide for the convenient insertion and removal of the cartridge 400.

With reference to FIG. 19, a further embodiment of the inserter 100a is illustrated therein and identified generally by the reference numeral 100b. The components of the inserter 100b that can be the same or similar to the inserter 100a are identified with the same reference numerals, except that a letter "b" has been added thereto.

With continued reference to FIG. 19, the energy storage portion 102b can be configured to use a compressive energy storage function of a coiled spring 500. The coiled spring can include a distal end 502 engaged with a piston 504 and a proximal end 506 held in place with a removable cap 256b. The piston 504 can be configured to form a seal, for example, with an O-ring 506, so as to operatively contain a substantially incompressible fluid in the chamber 202b. The remaining portions of the inserter 100b can be constructed in accordance with the description of the inserter 100a above.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:
1. An implant inserter comprising:
   a compressed gas storage portion comprising a compressed gas cartridge configured to release a compressed gas into the compressed gas storage portion;
   a hydraulic portion containing a substantially incompressible fluid;
   a piston disposed between the compressed gas cartridge and the hydraulic portion and configured to impart pressure of the released compressed gas in the compressed gas storage portion to the substantially incompressible fluid in the hydraulic portion;
   an actuator portion comprising a button or lever and a plunger mounted for sliding movement between a retracted position and an extended position, the actuator portion configured to allow a user to control a flow of the substantially incompressible fluid through the hydraulic portion to move the plunger from the retracted position to the extended position by using the button or lever; and
   an implant retaining portion comprising an implant for insertion into a treatment region of an animal and aligned with the plunger such that the plunger pushes the implant when the plunger moves from the retracted position toward the extended position.
2. The implant inserter of claim 1, wherein the compressed gas storage portion comprises a pressurized gas.

3. The implant inserter of claim 1, wherein the compressed gas cartridge comprises a two-phase pressurized material.

4. The implant inserter of claim 1, wherein the compressed gas storage portion further comprises a receiving portion.

5. The implant inserter of claim 4, wherein the receiving portion is sized to receive the compressed gas cartridge such that compressed gas cartridge can be contained in the implant inserter.

6. The implant inserter of claim 5, wherein the implant inserter further comprises a piercing needle, the piercing needle configured to pierce a seal on the compressed gas cartridge.

7. The implant inserter of claim 1, wherein the substantially incompressible fluid is positioned between the compressed gas storage portion and the plunger, the substantially incompressible fluid configured to transfer energy from the compressed gas storage portion to the plunger.

8. The implant inserter of claim 7, wherein the actuator portion further comprises a control portion with an actuator operably coupled to the button or lever, the control portion configured to control the flow of the substantially incompressible fluid from the compressed gas storage portion to the plunger.

9. The implant inserter of claim 8, wherein the actuator comprises an actuator rod, the actuator rod operably coupled to the button or lever at a first end and having an actuator piston at a second end, the actuator rod slidably translatable within the control portion.

10. The implant inserter of claim 7, wherein the piston comprises an accumulator piston contained in an accumulator piston chamber, the accumulator piston sealingly dividing the accumulator piston chamber into a first subchamber and second subchamber, the first subchamber in communication with the compressed gas storage portion and the second subchamber in communication with the substantially incompressible fluid.

11. The implant inserter of claim 10, wherein the implant inserter further comprises a plunger piston in a plunger piston chamber, the plunger piston sealingly in communication with the substantially incompressible fluid at a first end and connected to the plunger at a second end.

12. The implant inserter of claim 1, wherein the implant retaining portion is configured to receive an implant cartridge having an outer housing and the implant disposed therein.

13. The implant inserter of claim 12, wherein the implant retaining portion comprises a first distal end configured to engage a distal portion of the implant cartridge and a proximal end configured to engage a proximal portion of the implant cartridge.

14. The implant inserter of claim 12, wherein the implant retaining portion further comprises a sliding cartridge receiver, the sliding cartridge receiver configured to be slidably movable with respect to the actuator portion.

15. The implant inserter of claim 14, wherein the sliding cartridge receiver is configured to attach to a main body portion of the implant inserter and wherein the plunger is configured to extend into an implant cartridge, the plunger being slidably movable with respect to the implant cartridge.

16. The implant inserter of claim 1, wherein the implant comprises an ocular implant.

17. The implant inserter of claim 1, further comprising:
a needle portion; and
a throat portion, the needle portion configured to cooperate with the throat portion,
wherein the actuator portion is configured to allow the user to control the flow of the substantially incompressible fluid by displacing the needle portion from the throat portion to form a gap between the needle portion and the throat portion, the gap increasing with increasing displacement of the needle portion from the throat portion.

18. A method for discharging an implant from an implant cartridge, the method comprising:
providing the implant inserter of claim 1;
releasing stored energy from the compressed gas cartridge into the compressed gas storage portion;
transmitting the released energy from the compressed gas storage portion to the plunger and controlling translation of the plunger with the actuator portion.

19. The method of claim 18, wherein the step of transmitting the released energy from the compressed gas storage portion to the plunger comprises transmitting the released energy via the substantially incompressible fluid.

20. The method of claim 19, additionally comprising controlling the flow of the substantially incompressible fluid to the plunger.

21. The method of claim 18, wherein the implant comprises an ocular implant.

22. An implant inserter comprising:
an implant retaining portion comprising an implant;
a compressed gas storage portion comprising a compressed gas cartridge configured to release a compressed gas into the compressed gas storage portion;
a hydraulic portion containing a substantially incompressible fluid;
a piston disposed between the compressed gas cartridge and the hydraulic portion and configured to impart pressure of the released compressed gas in the compressed gas storage portion to the substantially incompressible fluid in the hydraulic portion;
an actuator portion comprising a plunger, the actuator portion communicating with the compressed gas storage portion and configured to allow a user to control a flow of the substantially incompressible fluid through the hydraulic portion to move the plunger via the substantially incompressible fluid for discharging the implant.

23. The implant inserter of claim 22, wherein the compressed gas storage portion comprises a pressurized gas.

24. The implant inserter of claim 22, wherein the compressed gas storage cartridge comprises a two-phase pressurized material.

25. The implant inserter of claim 22, wherein the actuator portion comprises at least one actuator configured to control a flow of the substantially incompressible fluid.

26. The implant inserter of claim 22, wherein the piston comprises a piston configured to transfer energy from the compressed gas storage portion to the substantially incompressible fluid.

27. The implant inserter of claim 22, wherein the implant is an ocular implant.

28. An implant inserter comprising:
an implant receiving portion comprising an implant for insertion into a treatment region of an animal;
a compressed gas storage portion comprising a compressed gas cartridge configured to release a compressed gas into the compressed gas storage portion;
a hydraulic portion containing a substantially incompressible fluid;
a piston disposed between the compressed gas cartridge and the hydraulic portion and configured to impart pressure of the released compressed gas in the compressed gas storage portion to the substantially incompressible fluid in the hydraulic portion;

a plunger configured to contact the implant and discharge the implant from the implant receiving portion; and a means for allowing a user to control a flow of the substantially incompressible fluid through the hydraulic portion to move the plunger.

29. The implant inserter of claim 28, wherein the implant is an ocular implant.

* * * * *